United States Patent
Merboth et al.

(10) Patent No.: US 7,045,141 B2
(45) Date of Patent: May 16, 2006

(54) ALLOGRAFT BONE COMPOSITION HAVING A GELATIN BINDER

(75) Inventors: Barbara L. Merboth, Bridgewater, NJ (US); Moon Hae Sunwoo, Old Tappan, NJ (US); Arthur A. Gertzman, Stony Point, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 611 days.

(21) Appl. No.: 10/150,097

(22) Filed: May 20, 2002

(65) Prior Publication Data

US 2002/0192263 A1 Dec. 19, 2002

Related U.S. Application Data

(63) Continuation-in-part of application No. 09/983,526, filed on Oct. 24, 2001, which is a continuation-in-part of application No. 09/515,656, filed on Feb. 29, 2000, now Pat. No. 6,437,018, which is a continuation-in-part of application No. 09/031,750, filed on Feb. 27, 1998, now Pat. No. 6,030,635, said application No. 09/515,656, is a continuation-in-part of application No. 09/365,880, filed on Aug. 3, 1999, now abandoned, which is a continuation of application No. 09/031,750.

(51) Int. Cl.
*A61F 2/00* (2006.01)

(52) U.S. Cl. ............... 424/423; 514/12; 514/21
(58) Field of Classification Search ............ 514/54.2; 424/423, 422, 426
See application file for complete search history.

(56) References Cited

U.S. PATENT DOCUMENTS

| | | | |
|---|---|---|---|
| 4,172,128 A | 10/1979 | Thiele et al. | |
| 4,191,747 A | 3/1980 | Scheicher | |
| 4,314,380 A | 2/1982 | Miyata et al. | |
| 4,440,750 A | 4/1984 | Glowacki et al. | |
| 4,485,096 A | 11/1984 | Bell | |
| 4,587,268 A | 5/1986 | Pfirrmann | |
| 4,678,470 A | 7/1987 | Nashef et al. | |
| 5,053,049 A | 10/1991 | Campbell | |
| 5,073,373 A | 12/1991 | O'Leary et al. | |
| 5,290,558 A | 3/1994 | O'Leary et al. | |
| 5,314,476 A | 5/1994 | Prewett et al. | |
| 5,356,629 A | 10/1994 | Sander et al. | |
| 5,422,340 A | * 6/1995 | Ammann et al. | 514/12 |
| 5,484,601 A | 1/1996 | O'Leary et al. | |
| 5,507,813 A | 4/1996 | Dowd et al. | |
| 5,510,418 A | * 4/1996 | Rhee et al. | 525/54.2 |
| 5,573,771 A | 11/1996 | Geistlich et al. | |
| 5,707,962 A | * 1/1998 | Chen et al. | 514/12 |
| 5,786,327 A | 7/1998 | Tam | |
| 5,830,493 A | 11/1998 | Yokota et al. | |
| 5,854,207 A | * 12/1998 | Lee et al. | 514/2 |
| 5,899,939 A | 5/1999 | Boyce et al. | |
| 5,972,368 A | 10/1999 | McKay | |
| 6,180,605 B1 | 1/2001 | Chen et al. | |
| 6,180,606 B1 | 1/2001 | Chen et al. | |
| 6,224,629 B1 | 5/2001 | Lin et al. | |
| 6,261,586 B1 | 7/2001 | McKay | |
| 6,294,187 B1 | 9/2001 | Boyce et al. | |
| 6,296,667 B1 | 10/2001 | Johnson et al. | |
| 6,311,690 B1 | 11/2001 | Jefferies | |
| 6,341,952 B1 | 1/2002 | Gaylo et al. | |
| 6,372,257 B1 | 4/2002 | Marchosky | |
| 6,432,710 B1 | 8/2002 | Boss, Jr. et al. | |
| 6,440,444 B1 | 8/2002 | Boyce et al. | |

OTHER PUBLICATIONS

U.S. Appl. No. 10/040,154, filed Oct. 22, 2001, McKay et al.
U.S. Appl. No. 09/922,909, filed Aug. 6, 2001, Frondoza et al.
U.S. Appl. No. 09/865,318, filed May 25, 2001, Wironen et al.
U.S. Appl. No. 09/792,681, filed Feb. 23, 2001, Long et al.
U.S. Appl. No. 09/789,292, filed Feb. 20, 2001, Donda et al.
U.S. Appl. No. 09/776,619, filed Feb. 2, 2001, Donda et al.
U.S. Appl. No. 09/776,404, filed Feb. 2, 2001, Wironen.
U.S. Appl. No. 09/014,519, filed Jan. 28, 1998, Wironen.
U.S. Appl. No. 08/816,079, filed Mar. 13, 1997, Wironen et al.
U.S. Appl. No. 08/422,745, filed Apr. 14, 1995, Jefferies.

* cited by examiner

*Primary Examiner*—James Spear
*Assistant Examiner*—Retford Berko
(74) *Attorney, Agent, or Firm*—John S. Hale; Gipple & Hale

(57) ABSTRACT

The invention is directed toward an osteoimplant for application to a bone defect site to promote new bone growth at the site which comprises a new bone growth inducing composition of demineralized allograft bone material mixed with an aqueous phosphate buffered gelatin which when lyophilized to remove water from the composition cross links the gelatin to form a solid structure.

39 Claims, No Drawings

ALLOGRAFT BONE COMPOSITION HAVING A GELATIN BINDER

RELATED APPLICATIONS

This is a continuation-in-part of U.S. patent application Ser. No. 09/983,526, filed Oct. 24, 2001, which is a continuation-in-part of U.S. patent application Ser. No. 09/515,656, filed Feb. 29, 2001 now U.S. Pat. No. 6,437,018 which is a continuation-in-part of U.S. patent application Ser. No. 09/031,750, filed Feb. 27, 1998 and issued into U.S. Pat. No. 6,030,635 on Feb. 29, 2000, the "656" Application also being a continuation-in-part of U.S. patent application Ser. No. 09/365,880, filed Aug. 3, 1999 now abandoned, which is a continuation application of U.S. patent application Ser. No. 09/031,750 which has issued into U.S. Pat. No. 6,030,635.

FIELD OF INVENTION

The present invention is generally directed toward a surgical bone defect filling product and more specifically is a composition using demineralized allograft bone particles mixed in a fluid carrier of phosphate buffered saline and gelatin with the gelatin being cross linked by lyophilization of the composition to form a solid composition for application to a bone defect area.

BACKGROUND OF THE INVENTION

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Many products have been developed in an attempt to develop bone deficit fillers. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. These inorganic materials are osteoconductive but are bioinert. The calcium sulfate materials absorb slowly but the other materials do not absorb or become remodeled into natural bone. They consequently remain in place indefinitely as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized and partially demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder having little to no residual calcium, averaging less than 0.01% and having a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material with a glycerol carrier to be "runny" and to flow away from the site almost immediately after placement; this prevents the proper retention of the bone material within the site as carefully placed by the surgeon. Furthermore concerns about the neurotoxic behavior of glycerol have been noted in Spine Vol. 26, No. 13 Jul. 1, 2001 in an editorial by the Deputy Editor, C. A. Dickman, M.D. which has a clinical recommendation to limit the dose of GRAFTON®, avoid use in certain medical situations, avoid use with small children and to avoid direct contact of GRAFTON® with exposed spinal nerves.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier.

U.S. Pat. No. 5,290,558 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813 and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues.

U.S. Pat. No. 5,356,629 discloses making a rigid gel in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, autogenous bone as well as other materials. The bioactive substance can also be an osteoinductive agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. However, the biocompatible particles used in this reference are used in a much greater weight ranging from 35% to 70% by weight then that taught by the present invention. The reference is directed toward a cement used for implantation of hip prosthesis and is not used to promote bone growth.

U.S. Pat. No. 5,830,493 is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no use of demineralization of bone.

U.S. Pat. No. 5,053,049 discloses a composition for treating bone defects comprising demineralized bone osteogenic powder that has been tanned and used with any suitable biologically compatible or inert carrier which may include polysaccharides. The tanning can be by glutaraldehyde or different agents including formaldehyde or alcohol.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35 C and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 4,191,747 teaches a bone defect treatment with coarsely ground, denatured bone meal freed from fat and ground into powder. The bone is not demineralized and retains its complete mineral content. The bone meal is mixed with a polysaccharide in a solution of saline and applied to the bone defect site.

U.S. Pat. No. 4,440,750 discloses the use of demineralized osteogenic bone powder in a physiological carrier such as saline to treat a bone defect site to promote new bone growth.

Another prior art product is the formulation of demineralized allograft bone particles in collagen. Both bovine and human collagen have been used for this application Bovine collagen carries the risk of an immunogenic reaction by the recipient patient. Recently, it has been found that a disease of cattle, bovine spongioform encephalopathy (mad cow disease) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

All of the previous noted products are in a paste or gel form and when set into a body cavity are shortly washed or carried away from the site by body fluids. An attempt to overcome this problem is set forth in U.S. Pat. No. 6,294,187 which discloses a compressed load bearing composition of bone particles with a bulk density of greater than about 0.7 g/cm3 and a wet compressive strength of at least about 3 MpA Accordingly, the prior art as embodied in the glycerol and other carrier based technology to deliver demineralized and mineralized allograft bone to a surgical osseous site is replete with problems and only partially addresses the problems inherent in the correcting surgical defects which are solved in the present invention.

SUMMARY OF THE INVENTION

The subject composition is a complex mixture of a partially demineralized bone matrix (DBM) mixed with a gelatin and saline phosphate buffer acting as a carrier for the agent, DBM. The composition is then lyophilized for 24 to 33 hours to remove from 90% to 99%+ of the water from the composition. The composition is cross linked by lyophilization to form a solid one fixation form which presents the DBM, and its bone morphogenetic proteins (BMP), and the macrostructure of the highly porous DBM itself to serve both as an osteoconductive matrix and to signal the patient's tissue and cells to initiate the growth of new bone (osteoinduction). The formulation is used primarily in contact with bleeding bone. This condition is created either from trauma or a surgical procedure, that may involve drilling, sawing, grinding or scraping the bone to achieve a bleeding condition. In surgery, the bone is traumatized or surgically cut exposing blood capillaries, Haversian canals (microchannels in the bone), periosteum (the protective tissue lining around bone), muscle and other structures in the surgical site, Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

In order for the DBM to be osteoinductive, interference either from the traumatized cells or the formulation must be at a minimum, i.e., a biocompatible condition should be established and maintained. Several specific properties have been established in the composition formulation to create a functional material. These properties pertain to both physical characteristics and to the achieving of a biocompatible or physiologically friendly condition.

It an object of the invention to provide a solid bone product which can be placed in the wound defect area and allows the bone defect to be remodeled.

It is an object of the invention to utilize a mineralized, partially demineralized or fully demineralized bone structure of a size that is useful to achieve the desired characteristics that maximizes the amount of bone in the formulation.

It is an additional object of the invention to use a gelatin and saline phosphate buffer carrier for the bone particles to present the composition in a state of physiological osmolality at the wound site.

It is also an object of the invention to create a bone defect material which can be easily handled by the physician and does not degenerate when contacting blood flow at the surgical site.

It is another object of the invention to create a bone defect material which does not interfere with healing at the wound site and promotes faster bone formation.

It is still another object of the invention to provide a preshaped bone defect form which can be used at the point of surgery.

DESCRIPTION OF THE INVENTION

The present invention and best mode is directed towards a partially demineralized bone material (DBM) composition having a residual calcium content ranging between about 3 to about 10%, preferably 4 to 6% mixed with a high molecular weight hydrogel and a phosphate buffer to heal bone defects. The term demineralization as used in relation to treatment of bone up through at least the middle of the 1990's was construed by those skilled in the art to mean that all or substantially all of the mineral content of bone was removed leaving the bone with a residual calcium approaching 0.0% but less than 0.01%. In the late 1990's the term demineralized was used to describe bone which had been subjected to demineralization and had a greater residual calcium content. The terms "fully demineralized" as applied to the bone particles refers to bone particles possessing less than 2%, preferably less than about 1% by weight percent of their original inorganic mineral content; "partially demineralized" is used to refer to bone after mineral removal, which has residual calcium left therein is in an amount of at least 3% by weight but less than 10% and "minimally demineralized" is used to refer to bone particles possessing at least about 90% by weight of their original inorganic mineral content. The unmodified term "demineralized" as applied to the bone particles is intended to cover any one or combinations of the foregoing described types of demineralized bone particles.

In the preferred embodiment, the DBM is prepared by soaking the bone segments for several minutes in a container with enough sterile ethanol to cover the tissue. The bone segments are milled and placed in a sieve to size the milled bone to 100–800 microns or coarse ground to achieve cortical/cancellous chips in the form of irregularly shaped polyhedra with an edge dimension up to 5 mm. The milled bone material is placed in mixing container and cleaned with a 5:1 ratio of 3% Hydrogen Peroxide and stirred for 15 minutes, removed and rinsed with a minimum of 3000 ml of sterile water. The rinsed bone powder is placed back into the cleaned mixing container and at least 1000 ml of 70% sterile ethanol is added and the solution is mixed for 30 minutes. The bone powder is then transferred into a No. 70 sieve and an open vacuum is applied to the bottom of the sieve and the bone powder is dried for 20 minutes. The dried bone powder is transferred to the demineralization process where it is weighed. The bone weight in grams is compared to a chart which determines the acid volume to be applied which is approximately 1 gram equals approximately 16 ml of acid. The bone powder is mixed with 0.6N HCl for about 2½ hours to achieve maximum bone powder surface engagement with the HCl to remove most of the mineral content. The bone powder can be left for a longer period of time to fully demineralize the bone powder.

When cortical/cancellous bone chips are used the bone chips are transferred to the demineralization process where the same is weighed. Bone chips are mixed with 0.6N HCl at a 1:16 ratio and treated for a longer time of up to 8 hours. Alternatively cortical/cancellous bone chips are mixed with 0.6N HCl which is calculated at a 1:30 ratio and treated for 3 to 5 hours to control the residual calcium content in the range of 4% to 8%. Similarity the bone chips can be left in acid for a longer period to time to achieve fully demineralized bone product.

The bone material is then rinsed with water and 800 ml of sodium phosphate dibasic buffer solution is added to the mixture and the mixture is stirred for about 1 hour to stabilized the pH at around 7.0. The buffered bone powder is then rinsed with sterile water several times leaving a preferred residual calcium content ranging from about 3.0% to about 8% by dry weight of the bone with an optimum preferred residual calcium content of 4% to 6%.

The combination of the respective sized components of demineralized, lyophilized, allograft bone when mixed with a carrier of PSB and gelatin produces a osteoinductive bone defect material which can be molded into any desired shape to form a solid construct. This construct is not readily dissolved and washed away by the blood and fluids at the wound site and thus will present osteoinductivity.

The amount of DBM is maximized to achieve the optimum balance of osteoinductivity and physical handling properties. Too much matrix bone creates a gritty or sandy condition in which the DBM is not ideally enclosed by the surrounding viscous matrix and the DBM bone particles would be too easily washed away. Conversely, if the bone concentration is too low, the osteoinductivity would be less than optimum. Bone concentration in the composition can be in the range of about 20% to about 50% prior to cross linking and from about 25% to about 65% after cross linking and gelatin is present in the range of about 20% to about 40% prior to cross linking and from about 25% to about 50% after cross linking upon completion of the lyophilization process. Lyophilization is conducted under conditions known in the art, namely an initial shelf temperature of from about −20° to about −55° C., preferably −40° C. for 4 hours, with the temperature raised to +35° C. for 28 hours, with the last 29 hours being under a vacuum of about 350 mTorr. The composition then sits at ambient temperature for 1 hour. The present invention can additionally use HA having a molecular weight of about $7.0 \times 10^5$–$3.0 \times 10^6$ Daltons. The present formulation uses a 700,000 Dalton molecular weight hydrogel (sodium hyaluronate or HA). The terms HA or sodium hyaluronate should be construed throughout this application as encompassing sodium hyaluronate, hyaluronic acid, pharmaceutically acceptable sats of hyaluronic acid, derivatives of hyaluronic acid and pharmaceutically acceptable salts of hyaluronic acid derivatives and mixtures thereof. This HA material is used at a 5–10% concentration in the gelatin and phosphate buffered saline.

Lesser molecular weight hydrogels can also be used. Such lesser weight hydrogels are 1) Chitosan about 10,000 to 300,000 Daltons; 2) Sodium Alginate about 10,000 to 300,000 Daltons; 3) Dextran about 40,000 Daltons; 4) carboxymethylcellulose (CMC) about 20,000 to 40,000 Daltons and 5) hydroxypropylmethylcellulose (HPMC) about 20,000 to 40,000 Daltons. Other non hydrogel substances which can be used are Gelatin and Collagen.

The natural condition for blood plasma as well as synovial fluid, cerebrospinal fluid, aqueous humor (fluid within the globe of the eye) is at a pH of 7.3–7.4 (reference, *Principles of Biochemistry*, Chapters 34 & 35; White, Handler and Smith, McGraw Hill, NY, 1964). At very slight changes in pH, blood cells will shift their equilibrium of hemoglobin. This hemoglobin concentration will change over the small pH range of 7.3 to 7.7 (White et al p. 664). In addition, at significantly lower pH values in the acidic range, protein molecules will denature, i.e., degrade. Thus, it is important to maintain any surgical implant which is intimate contact with blood at a biocompatible condition of about pH 7.2–7.4.

It is important to note that the body has many complex and redundant mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. It is a teaching of this invention that the preferred formulation will start out and maintain physiologic pH without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$. This buffer system is used to neutralize the acid to demineralize the bone. It is important to neutralize the acid (hydrochloric acid) used to demineralize the bone so as to assure that there is no residue of this very strong acid which could overwhelm the buffering capacity of the phosphate system.

The pH is adjusted to the physiologic 7.2–7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

The present invention uses sodium salts of the phosphate buffer. This is to create an equilibrium system at the wound site which will draw in calcium ions necessary to grow new bone. The mechanism to achieve this is based on the LeChatelier corollary to the *Principle of Chemical Equilibrium: When a factor (temperature, pressure, concentration, etc.) determining the equilibrium of a system is altered, the system tends to change in such a way as to oppose and partially annul the alteration in this factor.* (reference, *General Chemistry*, McCutcheon, Seltz and Warner, Van Nostrand, NY, 1944; p. 248).

The buffer solution will assist in stimulating the formation of bone growth at a bone defect site at a faster rate than a composition without such a buffer. Studies have shown that the presence of phosphate ions accelerates the formation of hydroxyapatite, the principle component of bone. Fulmer, M. T. et al "*Effects of Na2HPO4 and Na H2PO4 on hydroxyapatite formation,*" *J. Biomed. Maters, Res.*, Vol. 27 1095–1102 (1993)

This principal manifests at the bone wound site as follows: The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site. The bone regeneration mechanism will utilize calcium starting 7–10 days after the wound starts healing by the well-known osteochondral healing mechanism. Hence, the selection of the sodium phosphate buffer to achieve the physiologic pH provides a means to increase the calcium concentration in the precise location where calcium will be needed to grow new bone.

Thus, the invention induces the presence of soluble calcium at the bone defect site. This will encourage new bone growth through the normal biochemical mechanism. Soluble calcium can be attracted to the surgical site by using a sodium phosphate buffer of pH 6.8–7.2 in lieu of isotonic saline. The phosphate buffer attracts calcium cations to the site from the surrounding healthy bone and creates an equilibrium concentration of the calcium precisely at the site of healing where it is most desirable to grow new bone.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

Sodium hyaluronate in the form of the sodium salt is generally described as a glycosaniinoglycan (GAG). It is envisioned that suitable amounts of bone morphogenic proteins (BMP) can be added to the composition at any stage in the mixing process prior to lyophilization to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However, the amount of BMP varies in the bone depending on the age of the bone donor and the bone processing. Sterilization is an additional problem in processing human bone for medical use as boiling, autoclaving and irradiation over 2.0 Mrads is sufficient to destroy or alter the BMP present in the bone matrix.

In conducting experiments, it was found that a bone product with optimal molding and handling properties was obtained when a composition of demineralized allograft bone in a phosphate buffered saline and gelatin carrier was lyophilized to obtain a shaped or unshaped structure having cross linked gelatin and 25% to 65% demineralized bone content. The use of the term shaped as applied to the osteoimplant means a predetermined or regular form or configuration in contrast to an indeterminate or vague form or configuration and by way of example would be characteristic to a wedge, cylinder, disk, plate sheet, tube and the like.

Any number of medically usefill substances can be used in the invention by adding the substances to the composition at any steps in the mixing process or directly to the final composition. Such substances include collagen and insoluble collagen derivatives, hydroxy apatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin and silver salts. It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments and peptide growth factors, living cells such as chondrocytes, blood cells, bone marrow cells, mesenchymal stem cells, natural extracts, tissue transplants, bioadhesives, transforming growth factor (TGF-beta), platelet derived growth factor (PDGF), osteopontin, fibroblast growth factor (FGF), insulin-like growth factor (IGF-1); growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

EXAMPLES OF THE INVENTION

In the following examples, the components used are as follows:
1) Pharmaceutical grade gelatin
2) PBS (pH 7.38)—Type I water, monobasic sodium phosphate, dibasic sodium phosphate, sodium chloride
3) DBM
4) HA or sodium hyaluronate as defined above While various examples have been shown, the invention after lyophilization can have from 20% to 50% cross linked gelatin, 0.1 to 8% water, 0.5% to 3% residual monobasic sodium phosphate, dibasic sodium phosphate and sodium chloride and 20 to 65% DBM with the lyophilized structure having a pH running from 6.8 to 7.4.

In the preparation of PBS, for the invention:

1,000 ml Type I purified water (995 g) was placed on a stir plate. 1.8208 g of monobasic sodium phosphate monohydrate (J. T. Baker lot: 33152) was weighed and transferred into the Type I purified water in a bottle. 14.1541 g dibasic sodium phosphate heptahydrate (Mallinckrudt USP Lot: 7896N18595) was weighed and transferred into the bottle. See Table 1. 2.41904 g sodium chloride (J. T. Baker Lot M21474) was weighed and transferred into the bottle on the stir plate. The solution was mixed until all the salts were dissolved (minimum of 15 minutes).

TABLE 1

Components of PBS

| Component | Actual Weight |
|---|---|
| Monobasic sodium phosphate | 1.821 g |
| Dibasic sodium Phosphate | 14.154 g |
| Sodium Chloride | 2.419 g |

The pH meter (VWR brand model 3000 with Hamilton tiptrode electrode) was calibrated: % slope=96.1. The pH measured was: 7.35. Preparation of Gelatin mixtures (gelatin and PBS): The gelatin mixture for each formulation was prepared at the same time as each formulation. 12 weighing pans were labeled 1–12. 12–250 ml beakers were labeled 1–12. The water bath was turned on and the temperature set at 80° C. The second water bath (QC lab's) was filled partially using Type I water. The temperature was set on this water bath to 40° C. The appropriate amount of gelatin was weighed in each weighing pan. The appropriate weight of PBS was weighed in each beaker. The weights were recorded in Table 2.

TABLE 2

Weights of Components for Gelatin Mixtures

| Sample | Gelatin Mix Required for Formulation | Gelatin Weight | PBS Weight |
|---|---|---|---|
| 1 | 16 g | 4.872 g | 11.130 g |
| 2 | 14 g | 4.261 g | 9.742 g |
| 3 | 12 g | 3.651 g | 8.353 g |
| 4 | 12 g | 3.65 g | 8.351 g |
| 5 | 10 g | 3.042 g | 6.962 g |
| 6 | 10 g | 3.043 g | 6.961 g |
| 7 | 8 g | 2.430 g | 5.571 g |
| 8 | 8 g | 2.432 g | 5.571 g |
| 9 | 6 g | 1.832 g | 4.172 g |
| 10 | 6 g | 1.833 g | 4.174 g |
| 11 | See table 3 below | | |
| 12 | See table 3 below | | |

Note:
Formulation 11 was prepared with sodium hyaluronate and its derivatives (HA) and gelatin mixture composing 40% of the formulation. Formulation 12 was prepared with Gelatin mixture and glycerol.

TABLE 3

Preparation of Formulations 11 and 12 gelatin mixtures (8 g of each)

| Component | Formulation 11 Actual Weight | Formulation 12 Actual Weight |
|---|---|---|
| Gelatin | 2.432 g | 1.824 g |
| PBS | 3.571 g | 5.456 g |
| Glycerol | NA | 0.721 g |
| Paste HA | 2 g | NA |
| Total prepared | 6 g + 2 g | 8 g |

Table 4 is a description of the 12 samples of cross linked bone prepared.

TABLE 4

Description of Formulations

| Sample # | Gelatin Mixture | DBM | Paste HA |
|---|---|---|---|
| 1 | 80% | 20% | 0% |
| 2 | 70% | 20% | 10% |
| 3 | 60% | 40% | 0% |
| 4 | 60% | 30% | 10% |
| 5 | 50% | 50% | 0% |
| 6 | 50% | 40% | 10% |
| 7 | 40% | 60% | 0% |
| 8 | 40% | 40% | 20% |
| 9 | 30% | 70% | 0% |
| 10 | 30% | 60% | 10% |
| 11 | 40% | 60% | — |
| 12 | 40% | 60% | 0% |

Weighing pans were labeled 1–12. (weighing pans were labeled for the gelatin, DBM, and sodium hyaluronate or HA (when needed). A labeled beaker containing the weighed PBS was placed in the 80° C. water bath. The gelatin (in the appropriately labeled weighing pan) was transferred into a beaker in the water bath. The gelatin mixture was mixed with a spatula. The cover was placed on the water bath for approximately 5 minutes. After approximately 5 minutes, the cover was removed and the gelatin mixture was stirred until all the gelatin was dissolved (about 1–2 minutes of stirring after the 5 minutes). The beaker containing the gelatin mixture was transferred into the 40° C. water bath. The gelatin was continued to be stirred with a spatula in the 40° C. water bath for 1–2 minutes. The robo-thermometer was used to monitor the temperature of the gelatin. When the temperature of the gelatin reached about 40° C. (and remained constant), the DBM (and HA if required) were added to the gelatin. The weights were recorded in table 5.

TABLE 5

Actual Weights of components

| Sample # | Gelatin | DBM | HA | Grams of Gelatin Mix | Grams of DBM | Grams of HA | Total Prepared |
|---|---|---|---|---|---|---|---|
| 1 | 80% | 20% | 0% | 16.00 | 4.00 | 0 | 20 g |
| 2 | 70% | 20% | 10% | 14.00 | 4.00 | 2.00 | 20 g |
| 3 | 60% | 40% | 0% | 12.00 | 8.00 | 0 | 20 g |
| 4 | 60% | 30% | 10% | 12.00 | 6.00 | 2.00 | 20 g |
| 5 | 50% | 50% | 0% | 10.00 | 10.00 | 0 | 20 g |
| 6 | 50% | 40% | 10% | 10.00 | 8.00 | 2.00 | 20 g |
| 7 | 40% | 60% | 0% | 8.00 | 12.00 | 0 | 20 g |
| 8 | 40% | 40% | 20% | 8.00 | 8.00 | 4.00 | 20 g |
| 9 | 30% | 70% | 0% | 6.00 | 14.00 | 0 | 20 g |
| 10 | 30% | 60% | 10% | 6.00 | 12.00 | 2.00 | 20 g |
| 11* | 40% | 60% | 0% | 6.00 | 12.00 | 2.00 | 20 g |
| 12* | 40% | 60% | 0% | 8.00 | 12.00 | 0 | 20 g |

The formulation was mixed with a spatula until there wasn't any dry bone. The formulation was scooped from the beaker with a spatula and spread (evenly) over a microscope slide. Another slide was placed on top of the formulation. The two slides were evenly pressed together to form the desired thickness of the bone gel sample. The sample was allowed to cool (around room temperature). The edges sticking out of the slides were cut off using a scalpel. The top glass slide was carefully removed from the formulation. The formulation was removed from the bottom slide (it peeled right off the slide). Each formulation was placed into a zip lock bag labeled Gelatin formulation and #. Some formulations were too sticky to be placed on the glass slides. These formulations were "rolled out" with a 4-liter amber glass bottle. The rolled pieces were also cut with a scalpel into sheets. They were also placed in plastic bags labeled formulation number. Note: The formulations with the higher DBM concentrations appeared to be dry. Formulation 9 was so dry that all the DBM did not even mix with the gelatin mixture. The formulations with HA appeared mold better to a slide than the samples without HA. Table 6 shows the percentages of each formulation.

TABLE 6

Percentages of each component per formulation

| Sample | % Gelatin | % PBS | % DBM | % HA | % Glycerol | Total Prepared |
|---|---|---|---|---|---|---|
| 1 | 24.4% | 55.7% | 20% | 0% | 0% | 20 g |
| 2 | 21.3% | 48.7% | 20% | 10% | 0% | 20 g |
| 3 | 18.3% | 41.8% | 40% | 0% | 0% | 20 g |
| 4 | 18.3% | 41.8% | 30% | 10% | 0% | 20 g |
| 5 | 15.2% | 34.8% | 50% | 0% | 0% | 20 g |
| 6 | 15.2% | 34.8% | 40% | 10% | 0% | 20 g |
| 7 | 12.2% | 27.9% | 60% | 0% | 0% | 20 g |
| 8 | 12.2% | 27.9% | 40% | 20% | 0% | 20 g |
| 9 | 9.2% | 20.9% | 70% | 0% | 0% | 20 g |
| 10 | 9.2% | 20.9% | 60% | 10% | 0% | 20 g |
| 11 | 12.2% | 17.9% | 60% | 10% | 0% | 20 g |
| 12 | 9.1% | 27.3% | 60% | 0% | 3.6% | 20 g |

EXAMPLES

In each of the Examples 1 through 12, the samples (approximately 1"×1"×⅛") were lyophilized for 33 hours. After the freeze drying period, between 0.1 and 8% water were left in the lyophilized samples. While the DBM particle size was 250–812 micron, a size substitute of 100 to 850 microns would not change the composition.

Example 1

A Cross Linked Gelatin Bone Composition of 80% Gelatin Mixture and 20% DBM.

4.87 g of gelatin (Pharmaceutical grade gelatin) was mixed with 11.30 g PBS (phosphate buffered saline pH=7.35) in an 80° C. water bath until the mixture was uniform (gelatin was completely dissolved) for a total of 16 g of gelatin mixture. The gelatin mixture was cooled to 40° C. in a separate water bath. 4 g of DBM (demineralized bone matrix power—particle size 250–812 microns) was mixed (with a spatula) into the gelatin mixture (at 40° C.). The formulation was flattened, cooled to room temperature, and cut into sheets using a scalpel. A total of 20 g of gelatin bone was prepared consisting of 20% DBM in 80% gelatin mixture. The formulation was wet with PBS and evaluated before freeze-dried. This formulation was flexible, highly elastic, and had strong tare. After freeze drying, the tissue was re-hydrated with 10 ml PBS and by 40 minutes, the tissue form was completely flexible.

Example 2

A Cross Linked Gelatin Bone Formulation of 70% Gelatin Mixture, 20% DBM, and 10% Paste HA.

4.26 g of gelatin (Pharmaceutical grade gelatin) was mixed with 9.74 g PBS (phosphate buffered saline pH=7.35) in an 80° C. water bath until the mixture was uniform (gelatin was completely dissolved) for a total of 14 g of gelatin mixture. The gelatin mire was cooled to 40° C. in a separate water bath. 2 g of paste HA (Sodium Hyaluronate—paste carrier) was stirred into the gelatin mixture (at 40° C.). 4 g of DBM (demineralized bone matrix power—particle size 250–812 microns) was mixed (with a spatula) into the gelatin mixture with HA (at 40° C.). The formulation was flattened, cooled to room temperature, and cut into sheets using a scalpel. The gelatin bone formulation (20 g) consisted of 20% DBM, 70% gelatin mixture and 10% paste HA. The formulation was wet with PBS and evaluated before freeze-dried. Example 2 was nice and flexible. After freeze drying, the tissue was re-hydrated with 10 ml PBS and at 60 minutes, the tissue form was slightly flexible, intact, and uniform with a little loose bone at corners.

Example 3

A Cross Linked Gelatin Bone Formulation of 60% Gelatin Mixture and 40% DBM.

3.65 g of gelatin (Pharmaceutical grade gelatin) was mixed with 8.35 g PBS (phosphate buffered saline pH=7.35) in an 80° C. water bath until the mixture was uniform (gelatin was completely dissolved) for a total of 12 g of gelatin mixture. The gelatin mixture was cooled to 40° C. in a separate water bath. 8 g of DBM (demineralized bone matrix power—particle size 250–812 microns) was mixed (with a spatula) into the gelatin mire (at 40° C.). The formulation was flattened, cooled to room temperature, and cut into sheets using a scalpel. A total of 20 g of gelatin bone was prepared consisting of 40% DBM in 60% gelatin mire. The formulation was wet with PBS and evaluated before freeze-dried. Formulation 3 was very flexible, much thicker than examples 1 and 2, holds together nicely, and is stiffer and much less flexible than examples 1 and 2. After freeze drying, the tissue was re-hydrated with 10 ml PBS and at 60 minutes, it was very stiff and had loose bone around the corners.

Example 4

A Cross Linked Gelatin Bone Formulation of 60% Gelatin Mixture, 30% DBM, and 10% Paste HA.

3.65 g of gelatin (Pharmaceutical grade gelatin) was mixed with 8.35 g PBS (phosphate buffered saline pH=7.35) in an 80° C. water bath until the mixture was uniform (gelatin was completely dissolved) for a total of 12 g of gelatin mixture. The gelatin mixture was cooled to 40° C. in a separate water bath. 2 g of paste HA (Sodium Hyaluronate—paste carrier) was stirred into the gelatin mixture (at 40° C.). 6 g of DBM (demineralized bone matrix power—particle size 250–812 microns) was mixed (with a spatula) into the gelatin mixture with HA (at 40° C.). The formulation was flattened, cooled to room temperature, and cut into sheets using a scalpel. The gelatin bone formulation (20 g) consisted of 30% DBM, 60% gelatin mixture and 10% paste HA. The formulation was wet with PBS and evaluated before freeze-dried. Example 4 was much more flexible than example 3 and it was pretty strong and elastic. After freeze drying, the tissue was re-hydrated with 10 ml PBS and at 60 minutes, it was flexible, intact, and uniform.

Example 5

A Cross Linked Gelatin Bone Formulation of 50% Gelatin Mixture and 50% DBM.

3.04 g of gelatin (Pharmaceutical grade gelatin) was mixed with 6.96 g PBS (phosphate buffered saline pH=7.35) in an 80° C. water bath until the mixture was uniform (gelatin was completely dissolved) for a total of 10 g of gelatin mixture. The gelatin mixture was cooled to 40° C. in a separate water bath. 10 g of DBM (demineralized bone matrix power—particle size 250–812 microns) was mixed (with a spatula) into the gelatin mixture (at 40° C.). The formulation was flattened, cooled to room temperature, and cut into sheets using a scalpel. A total of 20 g of gelatin bone was prepared consisting of 50% DBM in 50% gelatin mixture. The formulation was wet with PBS and evaluated before freeze-dried. Example 5 was strong, but brittle and not flexible. The example cracked. After freeze drying, the tissue was re-hydrated with 10 ml PBS and at 60 minutes, the core piece was very stiff and it was breaking apart.

Example 6

A Cross Linked Gelatin Bone Formulation of 50% Gelatin Mixture, 40% DBM, and 10% Paste HA 3.04 g of gelatin (Pharmaceutical grade gelatin) was mixed with 6.96 g PBS (phosphate buffered saline pH=7.35) in an 80° C. water bath until the mixture was uniform (gelatin was completely dissolved) for a total of 10 g of gelatin mixture. The gelatin mixture was cooled to 40° C. in a separate water bath. 2 g of paste HA (Sodium Hyaluronate—paste carrier) was stirred into the gelatin mixture (at 40° C.). 8 g of DBM (demineralized bone matrix power—particle size 250–812 microns) was mixed (with a spatula) into the gelatin mixture with HA (at 40° C.). The formulation was flattened, cooled to room temperature, and cut into sheets using a scalpel. The gelatin bone formulation (20 g) consisted of 40% DBM, 50% gelatin mixture and 10% paste HA. The formulation was wet with PBS and evaluated before freeze-dried. Example 6 was flexible, pretty strong, and slightly brittle. After freeze drying, the tissue was re-hydrated with 10 ml PBS and at 60 minutes, it was slightly flexible with bone loosened around the ends.

Example 7

A Cross Linked Gelatin Bone formulation of 40% Gelatin mixture and 60% DBM.

2.43 g of Gelatin (Pharmaceutical grade Gelatin) was mixed with 5.57 g PBS (phosphate buffered saline pH=7.35) in an 80° C. water bath until the mixture was uniform (gelatin was completely dissolved) for a total of 8 g of gelatin mixture. The gelatin mixture was cooled to 40° C. in a separate water bath. 12 g of DBM (demineralized bone matrix power—particle size 250–812 microns) was mixed (with a spatula) into the gelatin mixture (at 40° C.). The formulation was flattened, cooled to room temperature, and cut into sheets using a scalpel. A total of 20 g of gelatin bone was prepared consisting of 60% DBM in 40% gelatin mixture. The formulation was wet with PBS and evaluated before freeze-dried. Example 7 was highly brittle. It was unacceptable. After freeze drying, the tissue was re-hydrated with 10 ml PBS and at 60 minutes, it was completely broken apart and started breaking apart at 15 minutes.

Example 8

A Cross Linked Gelatin Bone formulation of 40% Gelatin Mixture, 40% DBM, and 20% HA.

2.43 g of gelatin (Pharmaceutical grade gelatin) was mixed with 5.57 g PBS (phosphate buffered saline pH=7.35) in an 80° C. water bath until the mixture was uniform (gelatin was completely dissolved) for a total of 8 g of gelatin mixture. The gelatin mixture was cooled to 40° C. in a separate water bath. 4 g of paste HA (Sodium Hyaluronate—paste carrier) was stirred into the gelatin mixture (at 40° C.). 8 g of DBM (demineralized bone matrix power—particle size 250–812 microns) was mixed (with a spatula) into the gelatin mixture with HA (at 40° C.). The formulation was flattened, cooled to room temperature, and cut into sheets using a scalpel. The gelatin bone formulation (20 g) consisted of 40% DBM, 40% gelatin mixture and 20% paste HA. The formulation was wet with PBS and evaluated before freeze-dried. Example 8 was flexible and weak. After freeze drying, the tissue was re-hydrated with 10 ml PBS and at 60 minutes, it was disassembling with a lot of bone coming off of the piece.

Example 9

A Cross Linked Gelatin Bone Formulation of 30% Gelatin Mixture and 70% DBM.

1.83 g of Gelatin (Pharmaceutical grade Gelatin) was mixed with 4.17 g PBS (phosphate buffered saline pH=7.35) in an 80° C. water bath until the mixture was uniform (gelatin was completely dissolved) for a total of 6 g of gelatin mixture. The gelatin mixture was cooled to 40° C. in a separate water bath. 14 g of DBM (demineralized bone matrix power—particle size 250–812 microns) was mixed (with a spatula) into the gelatin mixture (at 40° C.). The formulation was flattened, cooled to room temperature, and cut into sheets using a scalpel. A total of 20 g of gelatin bone was prepared consisting of 70% DBM in 30% gelatin mixture. Example 9 was too dry to form into a sheet. It couldn't be formed and it returned to the powder form.

Example 10
A Cross Linked Gelatin Bone Formulation of 30% Gelatin Mixture, 60% DBM and 10% HA.

1.83 g of gelatin (Pharmaceutical grade gelatin) was mixed with 4.17 g PBS (phosphate buffered saline pH=7.35) in an 80° C. water bath until the mixture was uniform (gelatin was completely dissolved) for a total of 6 g of gelatin mixture. The gelatin mixture was cooled to 40° C. in a separate water bath. 2 g of paste HA (Sodium Hyaluronate—paste carrier) was stirred into the gelatin mixture (at 40° C.). 12 g of DBM (demineralized bone matrix power—particle size 250–812 microns) was mixed (with a spatula) into the gelatin mixture (at 40° C.). The formulation was flattened, cooled to room temperature, and cut into sheets using a scalpel. A total of 20 g of gel bone was prepared consisting of 60% DBM in 30% gelatin mixture and 10% HA. The formulation was wet with PBS and evaluated before freeze-dried. This formulation was too brittle. After freeze drying, the tissue was re-hydrated with 10 ml PBS and at 15 minutes, it started to break apart and at 60 minutes, it was almost completely broken apart.

Example 11
A Cross Linked Gelatin Bone Formulation of 40% Gelatin Mixture (15% Gelatin Mix and 25% HA) and 60% DBM.

2.43 g of gelatin (Pharmaceutical grade gelatin) was mixed with 3.57 g PBS (phosphate buffered saline pH=7.35) in an 80° C. water bath until the mixture was uniform (gelatin was completely dissolved) for a total of 6 g of gelatin mixture. The gelatin mixture was cooled to 40° C. in a separate water bath. 12 g of DBM (demineralized bone matrix power—particle size 250–812 microns) was mixed into the gelatin mixture (at 40° C.). 2 g of paste HA (Sodium Hyaluronate—paste carrier) was stirred into the gelatin mixture. 12 g of DBM (demineralized bone matrix power—particle size 250–812 microns) was mixed (with a spatula) into the gelatin mixture with HA (at 40° C.). The formulation was flattened, cooled to room temperature, and cut into sheets using a scalpel. The gelatin bone formulation (20 g) consisted of 60% DBM, 40% gelatin mixture (15% gelatin mix and 25% HA). The formulation was wet with PBS and evaluated before freeze-dried. Example 11 was very hard, brittle and strong. After freeze drying, the tissue was re-hydrated with 10 ml PBS and at 60 minutes, it was almost completely broken apart with clumps of bones in the PBS.

Example 12
A Cross Linked gelatin Bone Formulation of 40% Gelatin Mixture and Glycerol, 60% DBM.

1.824 g of gelatin (Pharmaceutical grade gelatin) was mixed with 5.456 g PBS (phosphate buffered saline pH=7.35) and 0.72 g of Glycerol in an 80° C. water bath until the mixture was uniform (gelatin was completely dissolved) for a total of 8 g of gelatin mixture. The gelatin mixture was cooled to 40° C. in a separate water bath. 12 g of DBM (demineralized bone matrix power—particle size 250–812 microns) was mixed into the gelatin mixture (at 40° C.). The formulation was flattened, cooled to room temperature, and cut into sheets using a scalpel. The gelatin bone formulation (20 g) consisted of 60% DBM, 40% gelatin mixture and glycerol. The formulation was wet with PBS and evaluated before freeze-dried. Example 12 was very brittle, weak and not flexible. After freeze drying, the tissue was re-hydrated with 10 ml PBS and at 60 minutes, it was almost completely broken apart with clumps of bone in the PBS.

Temperature differential of gelatin mixture when mixed with DBM resulted in no apparent change in the composition. The following Examples 13 through 15 did not show that the mixing temperature had any effect on product.

Example 13
A Cross Linked Bone Formulation of 50% Gelatin Mixture and 50% DBM.

3.04 g of gelatin (Pharmaceutical grade gelatin) was mixed with 6.96 g PBS (phosphate buffered saline pH=7.35) in an 80° C. water bath until the mixture was uniform (gelatin was completely dissolved) for a total of 10 g of gelatin mixture. The gelatin mixture was cooled to 70° C. in a separate water bath. 10 g of DBM (demineralized bone matrix power—particle size 250–812 microns) was mixed (with a spatula) into the gelatin mixture (at 70° C.). The formulation was flattened, cooled to room temperature, and cut into sheets using a scalpel. A total of 20 g of gel bone was prepared consisting of 50% DBM in 50% gelatin mixture.

Example 14
A Cross Linked gelatin Formulation of 50% Gelatin Mixture and 50% DBM.

3.04 g of gelatin (Pharmaceutical grade gelatin) was mixed with 6.96 g PBS (phosphate buffered saline pH=7.35) in an 80° C. water bath until the mixture was uniform (gelatin was completely dissolved) for a total of 10 g of gelatin mixture. The gelatin mixture was cooled to 60° C. in a separate water bath. 10 g of DBM (demineralized bone matrix power—particle size 250–812 microns) was mixed (with a spatula) into the gelatin mixture (at 60° C.). The formulation was flattened, cooled to room temperature, and cut into sheets using a scalpel. A total of 20 g of gel bone was prepared consisting of 50% DBM in 50% gelatin mixture.

Example 15
A Cross Linked Gelatin Formulation of 50% Gelatin Mixture and 50% DBM.

3.04 g of gelatin (Pharmaceutical grade gelatin) was mixed with 6.96 g PBS (phosphate buffered saline pH=7.35) in an 80° C. water bath until the mixture was uniform (gelatin was completely dissolved) for a total of 10 g of gelatin mixture. The gelatin mixture was cooled to 50° C. in a separate water bath. 10 g of DBM (demineralized bone matrix power—particle size 250–812 microns) was mixed (with a spatula) into the gelatin mixture (at 50° C.). The formulation was flattened, cooled to room temperature, and cut into sheets using a scalpel. A total of 20 g of gel bone was prepared consisting of 50% DBM in 50% gelatin mixture.

A number of tests were performed to ascertain maximum DBM concentration which could be mixed to form the composition. A ratio of 70:30 (DBM to GELATIN CARRIER) was found to be unacceptable and the mix could not be flattened because it would not hold together.

The following examples were formed with pharmaceutical grade gelatin Batch #: 90611. Glycerol Anhydrous—J. T. Baker lot: K02640. DBM lots: 490020, 890020.

Example 16
A Cross Linked Gelatin Bone Formulation of 60% Gelatin Mixture and 40% DBM.

5.5 g of gelatin (Pharmaceutical grade gelatin) was mixed with 12.5 g PBS (phosphate buffered saline pH=7.35) in an 80° C. water bath until the mixture was uniform (gelatin was completely dissolved) for a total of 18 g of gelatin mixture. 12 g of DBM (demineralized bone matrix power—particle size 250–812 microns) was mixed into the gelatin mixture (at 80° C.). The formulation was flattened, cooled to room temperature, and cut into sheets using a scalpel. The gelatin bone formulation (30 g) consisted of 40% DBM and 60% gelatin mixture. The formulation was wet with PBS and evaluated before freeze-dried. Example 16 was very flexible and strong. After freeze drying, the tissue was re-hydrated with 10 ml PBS and it was very stiff at 60 minutes, flexible and intact at 4 hours.

Example 17
A Cross Linked Gelatin Bone Formulation of 50% Gelatin Mixture and 50% DBM.

4.6 g of gelatin (Pharmaceutical grade gelatin) was mixed with 10.4 g PBS (phosphate buffered saline pH=7.35) in an 80° C. water bath until the mixture was uniform (gelatin was completely dissolved) for a total of 15 g of gelatin mixture. 15 g of DBM (demineralized bone matrix power—particle size 250–812 microns) was mixed into the gelatin mixture (at 80° C.). The formulation was flattened, cooled to room temperature, and cut into sheets using a scalpel. The gelatin bone formulation (30 g) consisted of 50% DBM and 50% gelatin mixture. The formulation was wet with PBS and evaluated before freeze-dried. Example 17 was less flexible than Example 16, but was still strong enough. After freeze drying, the tissue was re-hydrated with 10 ml PBS and at 60 minutes, there was a little loose bone but it was very stiff at 4 hours, it was less uniform and somewhat flexible.

Example 18
A Cross Linked Gelatin Bone Formulation of 60% Gelatin Mixture (with Glycerol) and 40% DBM.

3.41 g of gelatin (Pharmaceutical grade gelatin) was mixed with 10.23 g PBS (phosphate buffered saline pH=7.35) and 1.36 g of glycerol in an 80° C. water bath until the mixture was uniform (gelatin was completely dissolved) for a total of 15 g of gelatin mixture. 10 g of DBM (demineralized bone matrix power—particle size 250–812 microns) was mixed into the gelatin mixture (at 80° C.). The formulation was flattened, cooled to room temperature, and cut into sheets using a scalpel. The gelatin bone formulation (25 g) consisted of 40% DBM and 60% gelatin mixture. The formulation was wet with PBS and evaluated before freeze-dried. Example 18 was stiffer than Examples 16 and 17 and less elastic, but still flexible and strong enough. After freeze drying, the tissue was re-hydrated with 10 ml PBS and at 60 minutes, there were a little loose bone, very stiff at 4 hours, slightly soft cracks when bent, it was disintegrated.

Example 19
A Cross Linked Gelatin Formulation of 50% Gelatin Mixture (with Glycerol) and 50% DBM.

3.41 g of gelatin (Pharmaceutical grade gelatin) was mixed with 10.23 g PBS (phosphate buffered saline pH=7.35) and 1.36 g of glycerol in an 80° C. water bath until the mixture was uniform (gelatin was completely dissolved) for a total of 15 g of gelatin mixture. 10 g of DBM (demineralized bone matrix power—particle size 250–812 microns) was mixed into the gelatin mixture (at 80° C.). The formulation was flattened, cooled to room temperature, and cut into sheets using a scalpel. The gel bone formulation (25 g) consisted of 40% DBM and 60% gelatin mixture. The formulation was wet with PBS and evaluated before freeze-dried. Example 19 was nice, flexible and strong. After freeze drying, the tissue was re-hydrated with 10 ml PBS and after 60 minutes when the flexibility was tested, it broke apart.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

We claim:

1. A sterile bone repair composition for application to a bone defect site to promote new bone growth at the site comprising a mixture of allograft osteoinductive bone material which is at least partially demineralized in a carrier forming a composition, the bone material ranging from about 20% to about 65% of the weight of the composition and the carrier comprising a gelatin component dissolved in an aqueous solution containing a hydrogel, said composition being lyophilized to achieve a crosslinking of the gelatin to obtain a structural stability which is maintained after application to said bone defect site, said gelatin comoonent ranting from about 10% to about 50% by weight of the composition after lyophilization.

2. A sterile bone repair composition as claimed in claim 1 wherein said mixture includes bone morphogenic protein in excess of the amount naturally occurring in allogeneic bone.

3. A sterile bone repair composition as claimed in claim 1 wherein said osteoinductive bone material is demineralized with a calcium content below about 1%.

4. A malleable bone composition as claimed in claim 1 wherein said gelatin carrier includes a phosphate buffered saline with a pH ranging from 7.0 to about 7.4.

5. A malleable bone composition as claimed in claim 1 wherein said bone material is partially mineralized with a calcium content between about 4% to about 8%.

6. A sterile bone repair composition as claimed in claim 1 wherein said aqueous solution comprises at least one ofa group consisting of water, saline and phosphate buffered saline.

7. A sterile bone repair composition as claimed in claim 1 wherein said hydrogel is selected from the group consisting of sodium hyaluronate and its derivatives, chitosan, sodium alginate, dextran, carboxymethylcellulose (CMC) and hydroxypropylmethylcellulose (HPMC).

8. A sterile bone repair composition as claimed in claim 1 wherein said allograft aqueous solution has a pH ranging from about 7.0 to about 7.4.

9. A sterile bone repair composition as claimed in claim 1 wherein said bone material includes bone particles ranging from 100 microns to 850 microns in size.

10. A sterile bone repair composition as claimed in claim 1 wherein said bone material contains growth factors transforming growth factor (TGF-beta), platelet derived growth factor (PDGF), osteopontin, fibroblast growth factor (FGF) and insulin-like growth factor (IGF-1).

11. A sterile bone repair composition for application to a bone defect site to promote new bone growth at the site comprising a mixture of allogeneic osteoinductive bone material which is partially demineralized and has a residual calcium content ranging from about 4.0% to about 8.0% in an aqueous gelatin carrier, said aqueous gelatin carrier contains a gelatin component and a hydrogel component, said hydrogel component comprising at least one of a group consisting of sodium hyaluronate and its derivatives, chitosan, sodium alginate, dextran, carboxymethylcellulose (CMC) and hydroxypropylmethylcellulose (HPMC) which is lyophilized to remove the water content leaving a crosslinked gelatin bone structure having a structural stability which is maintained alter application to said bone repair site, with said bone material ranging from about 30% to about 60% of the weight of the composition and said gelatin component ranging from about 30% to about 60% by weight of the composition.

12. A sterile bone repair composition as claimed in claim 11 wherein said aqueous gelatin contains a phosphate buffered saline with a pH ranging from 7.0 to about 7.4.

13. A sterile bone repair composition as claimed in claim 12 wherein phosphate in said phosphate buffered saline includes at least two phosphate ions $HPO_4^{-2}$ and $H_2PO_4^{-1}$.

14. A sterile bone repair composition as claimed in claim 11 including antimicrobial and/or antibiotics erythromycin, bacitracin, neomycin, penicillin, polymyxin B, tetracycline, viomycin, chloromycetin and streptomycin, cefazolin, ampicillin, azactam, tobramycin, clindamycin, gentamycm and vitamins.

15. A sterile bone repair composition as claimed in claim 11 wherein said composition includes bone morphogenic proteins in excess of the amount naturally occurring in allogeneic bone.

16. A sterile bone repair composition as claimed in claim 11 wherein said composition has a pH ranging from 6.8 to 7.4.

17. A sterile bone repair composition as claimed in claim 11 wherein said bone material contains growth factors transforming growth factor (TGF-beta), platelet derived growth factor (PDGF), osteopontin, fibroblast growth factor (FGF) and insulin-like growth factor (IGF-1).

18. A sterile bone repair composition for application to a bone defect site to promote new bone growth at the site comprising new bone growth inducing partially demineralized lyophilized allograft bone material having a particle size ranging from about 100 to about 850 microns mixed in an aqueous gelatin carrier, containing a hydrogel component ranging from 5% to 10% by weight to form a composition which is lyophilized to remove water content leaving a crosslinked gelatin bone structure having a structural stability which is maintained after application to said bone defect site with said bone material ranging from about 30% to about 50% of the weight of the composition of the structure and the crosslinked gelatin ranging from 30% to 60% by weight of the composition of the structure.

19. A sterile bone repair composition as claimed in claim 18 wherein said hydrogel component comprises at least one ofa group consisting of sodium hyaluronate and its derivatives, chitosan, sodium alginate, dextran, carboxymethylcellulose (CMC) and hydroxypropylmethylcellulose (HPMC).

20. A sterile bone repair composition for application to a bone defect site to promote new bone growth at the site which comprises a new bone growth inducing compound of partially demineralized lyophilized allograft bone material with a calcium content greater than 4% and less than 8% dry weight and a particle size ranging from about 100 to about 850 microns mixed in an aqueous gelatin carrier having a hydrogel component comprising a glycosaminoglycan ranging from about 5.0% to about 15.0% by weight of the composition and having a molecular weight of at least 700,000 Daltons, said mixture being lyophilized to remove water content with the water content after lyophilization ranging from about 0.1% to about 1.0% leaving a crosslinked gelatin bone structure having a structural stability which is maintained after application to said bone repair site with said bone material ranging from about 30% to about 50% of the weight of the composition and the crosslinked gelatin ranging from 30% to 60% by weight of the composition.

21. A sterile bone repair composition as claimed in claim 20 wherein said glycosaminoglycan is sodium hyaluronate and its derivatives.

22. A sterile bone repair composition as claimed in claim 20 wherein said aqueous gelatin carrier includes a phosphate buffered saline.

23. An osteoimplant as claimed in claim 20 wherein said glycosaminoglycan is selected from a group consisting of sodium hyaluronate and its derivatives, chitosan, sodium alginate, dextran, carboxymethylcellulose (CMC) and hydroxypropylmethylcellulose (HPMC).

24. An osteoimplant for application to a bone defect site to promote new bone growth at the site which comprises a new bone growth inducing compound of demineralized allograft osteoinductive bone material mixed in a phosphate buffered aqueous gelatin carrier which is lyophilized to remove water content leaving a crosslinked gelatin bone structure having a structural stability which is maintained after application to said bone repair site, said bone material ranging from about 30% to about 60% of the weight of the structure and the crosslinked gelatin ranging from 30% to 60% by weight of the structure with the water content of said structure ranging from about 0.1% to about 1.0%.

25. A method as claimed in claim 24 wherein said osteoinductive bone material is powdered bone ranging from about 100 microns to about 850 microns.

26. A method as claimed in claim 24 wherein said osteoinductive bone material is powdered bone with a residual calcium content ranging from about 4% to about 8%.

27. A method as claimed in claim 24 wherein said osteoinductive bone material is powdered bone which has been deniineralized to have a residual calcium content which is less than 1%.

28. A method as claimed in claim 24 wherein said osteoinductive bone material includes mineralized bone chips.

29. A method of constructing a crosslinked osteoinductive bone repair construct comprising the steps of:
   a. dissolving a gelatin in an aqueous solution;
   b. mixing osteoinductive bone material in an aqueous solution and gelatin mixture to obtain a formulation;
   c. shaping said formulation into a specific shape; and
   d. subjecting said shaped formulation to lyophilization at a negative temperature to remove at least 90% of water from said aqueous gelatin osteoinductive bone mixture crosslinking said gelatin and osteoinductive bone material contained therein to form a solid structure.

30. A method as claimed in claim 29 wherein said aqueous solution comprises at least one of a group consisting of phosphate buffered saline, saline and water.

31. A method as claimed in claim 29 wherein said aqueous solution includes a hydrogel component of less than 10% by weight.

32. A method as claimed in claim 31 wherein said hydrogel component comprises at least one of a group consisting of sodium hyaluronate and its derivatives, chitosan, sodium alginate, dextran, carboxymethylcellulose (CMC) and hydroxypropylmethylcellulose (HPMC).

33. A method as claimed in claim 29 wherein said aqueous solution has a pH ranging from about 7.0 to about 7.4.

34. A method of constructing a crosslinked osteoinductive bone repair construct comprising the steps of:
   a. dissolving a gelatin in an aqueous solution;
   b. mixing from about 20% to about 50% by weight osteoinductive bone material in an aqueous gelatin and hydrogel mixture to obtain a bone repair formulation, said hydrogel being less than 10% by weight of said formulation;
   c. shaping said bone repair formulation into a specific shape for; and
   d. lyophilizing said shaped bone repair formulation below 0° C. for a period of time sufficient to leave from 0.01 to 0.8% water in said aqueous gelatin osteoinductive bone formulation and crosslink said gelatin with said osteoinductive bone material contained therein to form a solid structure with said gelatin ranging from about 30% to about 60% fo the weight of the structure.

35. A method as claimed in claim 34 wherein said aqueous solution comprises at least one of a group consisting of phosphate buffered saline, saline and water.

36. A method as claimed in claim 34 wherein said lyophilization is at −40° C. for about 4 hours.

37. A method of constructing a crosslinked osteoinductive bone repair construct comprising the steps of:
 a. dissolving a gelatin in an aqueous solution containing a glycosaminoglycan;
 b. mixing osteoinductive demineralized bone material having a size ranging from 100 microns to 2 mm and 30% to 60% by weight in said aqueous gelatin solution to obtain a formulation;
 c. shaping said formulation into a specific shape; and
 d. subjecting said shaped formulation to lyophilization at a temperature of at least −40° C. to remove at least 92% of water from said aqueous gelatin osteoinductive bone mixture crosslinking said gelatin, glycosaminoglycan and osteoinductive demineralized bone material contained therein to form a solid structure.

38. A method as claimed in claim 37 wherein said lyophilization of step d, is conducted for at least 4 hours after which the temperature is raised to about +35° C. for 20 to 28 hours with the formulation at the higher temperature being placed under a vacuum of about 350 mTorr.

39. A method as claimed in claim 37 wherein about 0.1 to about 8% of the original water is left in the formulization after lyophilization.

* * * * *

UNITED STATES PATENT AND TRADEMARK OFFICE
CERTIFICATE OF CORRECTION

| | | |
|---|---|---|
| PATENT NO. | : 7,045,141 B2 | |
| APPLICATION NO. | : 10/150097 | |
| DATED | : May 16, 2006 | |
| INVENTOR(S) | : Barbara L. Merboth, Moon Hae Sunwoo and Arthur A. Gertzman | |

It is certified that error appears in the above-identified patent and that said Letters Patent is hereby corrected as shown below:

In column 18, line 14, replace the word "comoonent" with the word --component--;

In column 18, line 15, replace the word "ranting" with the word --ranging--;

In column 18, line 31, replace the word "ofa" with the words --of a--;

In column 20, line 26, replace the word "deniineralized" with the word --demineralized--;

In column 21, line 5, replace the word "fo" with the word --of--; and

In column 22, line 15, replace the word "formulization" with the word --formulation--.

Signed and Sealed this
Seventh Day of June, 2011

David J. Kappos
*Director of the United States Patent and Trademark Office*